United States Patent [19]

Bees et al.

[11] Patent Number: 5,313,822
[45] Date of Patent: May 24, 1994

[54] METHOD AND APPARATUS FOR PRESSURE TESTING LARGE VESSELS

[75] Inventors: William J. Bees, Wadsworth; Dennis K. McDonald, Massillon, both of Ohio

[73] Assignee: The Babcock & Wilcox Company, New Orleans, La.

[21] Appl. No.: 911,371

[22] Filed: Jul. 13, 1992

Related U.S. Application Data

[63] Continuation-in-part of Ser. No. 725,845, Jul. 3, 1991, abandoned.

[51] Int. Cl.$^5$ ............................................. G01M 3/02
[52] U.S. Cl. ........................................ 73/37; 73/49.2; 73/49.8
[58] Field of Search ............... 73/37, 40, 49.2, 49.8, 73/46; 376/294, 304; 220/584, 581; 976/DIG. 166

[56] References Cited

U.S. PATENT DOCUMENTS 3,653,434  4/1972  Andersson ..................... 376/294

Primary Examiner—Hezron E. Williams
Assistant Examiner—Michael Brock
Attorney, Agent, or Firm—Robert J. Edwards

[57] ABSTRACT

A method and apparatus for pressure testing a large vessel utilizing a base enclosure having a base ring of the same diameter as the pressure vessel. The base enclosure includes a base plate welded to the base ring and beams under the base plate for supporting the weight of the base enclosure as well as the portion of the vessel to be tested. The vessel is fabricated in or divided into half portions with each portion being connected to a base ring for separate testing. This eliminates the excessive weight that would be experienced if the vessel were to be pressure tested as one unit, particularly in the case of hydrotesting where the vessel is filled with water.

18 Claims, 2 Drawing Sheets

METHOD AND APPARATUS FOR PRESSURE TESTING LARGE VESSELS

This is a continuation-in-part of application Ser. No. 07/725,845 filed Jul. 3, 1991, now abandoned.

FIELD AND BACKGROUND OF THE INVENTION

The present invention relates, in general, to pressure testing or hydrotesting of large vessels.

Many industrial processes utilize pressure vessels of ever increasing size. One example is the large vessel used in pressurized fluidized bed reactors.

Large pressure vessels are currently hydrotested using immense quantities of water for test purposes. The vessels are set on concrete and steel base rings that were carefully positioned over floor piles, to provide sufficient support for the weight of the large vessel and the water contained therein. FIG. 1 is a side elevation view of such a vessel 2 which may have a height of 100 feet and a diameter of 60 feet. To pressure test this vessel, it must be supported on a strong foundation 4. Because of the size and weight of the vessel as well as the water in the vessel during hydrotesting, such tests are very expensive and difficult to conduct.

SUMMARY OF THE INVENTION

The present invention comprises a method and an apparatus which makes it possible to pressure test extremely large vessels, in a more economical and practical manner.

According to the present invention, the large pressure vessel is fabricated in or divided into separate portions which are independently pressure tested using a base enclosure for each portion. The separately tested portions are thereafter connected or reconnected to each other, preferably at a site where the vessel will ultimately be used. This not only has the advantage of permitting the separate pressure testing of smaller and less heavy structures than the fully assembled vessel, but also expedites shipping of the vessel in parts, specifically the portions into which the vessel was fabricated or divided for pressure testing.

Accordingly, an object of the present invention is to provide a method of pressure testing a large vessel, comprising fabricating or dividing the vessel into a first portion having one closed end and an opposite open end, and a second portion having one closed end and an opposite open end; attaching a base enclosure to the open end of the first portion for closing the open end of the first portion; attaching a base enclosure to the open end of the second portion for closing the open end of the second portion; separately pressure testing the first and second portions of the vessel; subsequently disconnecting the base enclosures from the first and second portions for reopening the open ends of the first and second portions; and connecting or reconnecting the first and second portions of the vessel at their open ends for assembling or reassembling the vessel.

A further object of the present invention is to provide an apparatus for pressure testing a large vessel, comprising a base ring having an upper edge adapted to be attached to an open end of a vessel portion for testing the vessel portion, the base ring having a lower edge; a base plate connected to the lower edge of the base ring to form a base enclosure with the base ring; inlet/outlet means connected to the base enclosure for admitting and releasing pressure fluid into and out of the base enclosure for pressure testing a vessel portion attached to the base ring; and support means connected to the base plate for supporting the weight of the base enclosure, a vessel portion to be pressure tested and a fluid contained in the vessel portion for use in the pressure test.

A further object of the present invention is to provide an apparatus for testing large vessels which is simple in design, rugged in construction and economical to manufacture.

The various features of novelty which characterize the invention are pointed out with particularity in the claims annexed to and forming a part of this disclosure. For a better understanding of the invention, its operating advantages and the specific objects attained by its uses, reference is made to the accompanying drawings and descriptive matter in which the preferred embodiments of the invention are illustrated.

DESCRIPTION OF THE PREFERRED EMBODIMENTS

Figure 1:
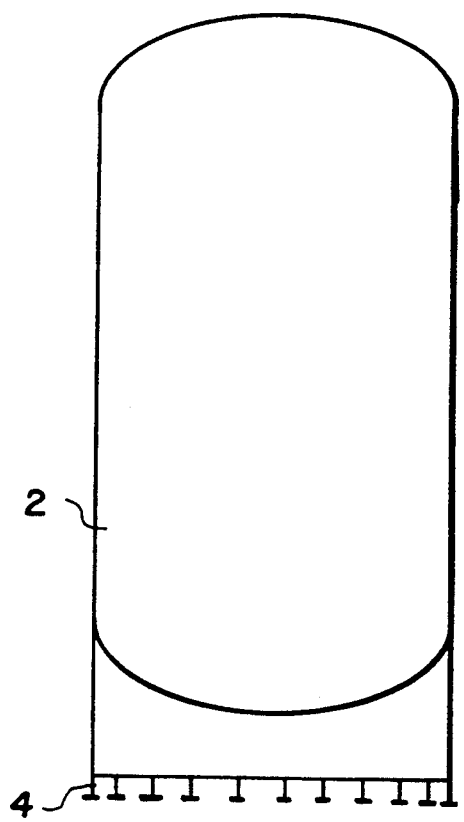
FIG. 1 is a side elevation view of a large vessel and a known support arrangement for pressure testing the vessel.
Figure 2:
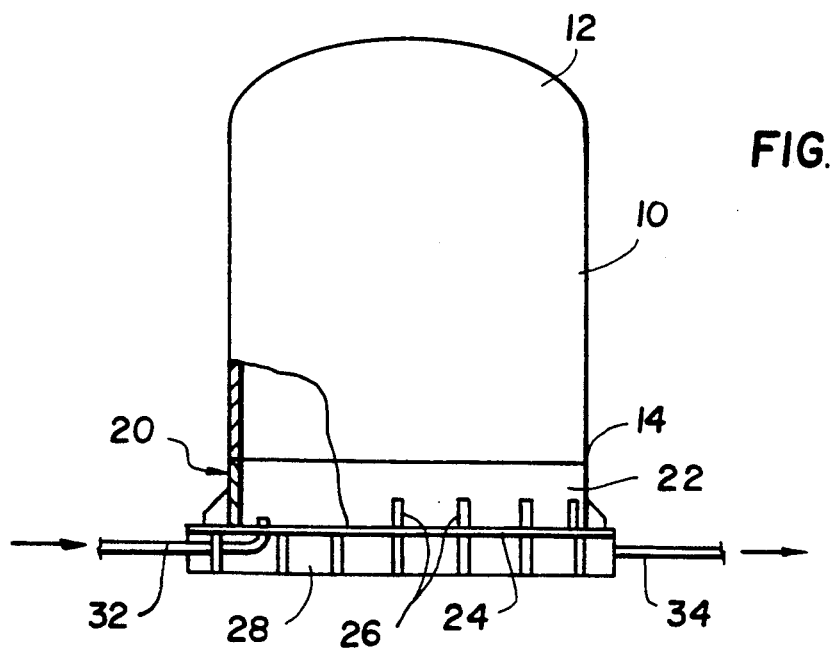
FIG. 2 is a side elevation view of the top half of a large vessel which is being pressure tested in accordance with the present invention.

Referring to the drawings in particular, the invention embodied in FIG. 2 comprises a method and apparatus for pressure testing a large vessel. According to the present invention, the vessel is fabricated in or divided into first and second portions. In the case of FIG. 2, the first portion comprises the upper half 10 of the pressure vessel which has a closed upper end 12 and a lower open end or rim 14 defined by the great circle which was formed when the cylindrical body of the vessel was cut in half. In accordance with the present invention, a reusable base enclosure generally designated 20 is welded to the open rim 14 of the vessel portion 10 for reclosing the vessel portion so that it can be pressure tested. While ideally the vessel-to-base enclosure weld at 14 is identical to the vessel shell section welds (not shown) which form the vessel portion 10, since the weld at ring 14 is temporary, it need not be a full penetration weld nor must it pass the more rigorous weld testing requirements of the remaining vessel welds (e.g. NDT). The weld at 14 must however conform in strength and efficiency to the remaining vessel welds to avoid a failure at the temporary weld during pressure testing.

As shown in FIG. 2, base enclosure 20 comprises a cylindrical base ring 22 having an upper edge to be welded at 14 to the upper vessel half and a lower edge that is welded to a circular base plate 24 which closes the lower end of the base enclosure. Gussets 26 welded between the outer surface of the base ring 22 and the base plate 24 further reinforce the enclosure.

To better distribute the weight of the vessel during the pressure test, support means in the form of support beams 28 are welded to the lower surface of base plate 24.

In order to actually conduct the test, inlet/outlet means are connected to the base enclosure 20 for admitting and draining a pressure fluid such as water for a hydrotest or air for a pneumatic test. The inlet/outlet means comprise an inlet conduit or pipe 32 which extends through the base plate 24 into the interior of enclosure 20 and thus into the interior of the vessel portion 10. After the pressure test, the fluid is drained or released from vessel portion 10 through an outlet conduit or pipe 34 which also opens through base plate 24. Alternatively, the inlet and outlet conduits or pipes can extend through the base ring 22.

Figure 3:
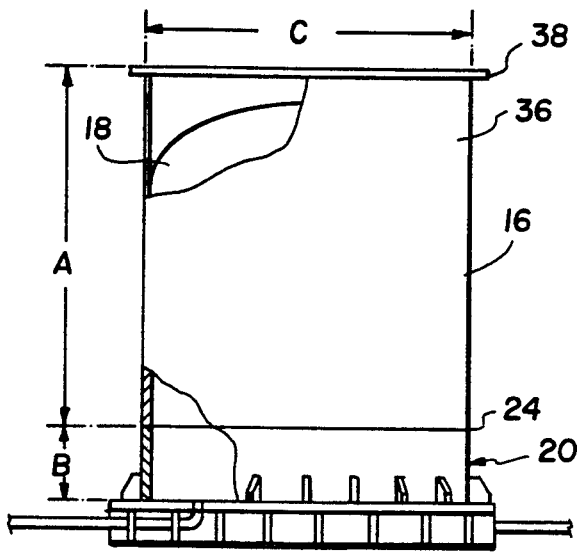
FIG. 3 is a view similar to FIG. 2 of the bottom half of the pressure vessel.

FIG. 3 illustrates an arrangement which is analogous to that of FIG. 2, but for testing the lower half 16 of the vessel. As with the upper half of the vessel, when the vessel is fabricated or divided, the lower half continues to have one closed end 18, this time the bottom, and an opposite open end in the form of a great circle or rim 24 to which the base enclosure 20 is welded. In FIG. 3, the same reference numbers are utilized to designate the same or similar parts as those in FIG. 2. The base enclosure 20 in FIG. 3 is advantageously of identical design to the base enclosure 20 in FIG. 2.

FIG. 3 also illustrates a skirt portion 36 and vessel plate 38 which are part of the bottom half of the vessel. As shown in FIG. 3, for conducting the pressure test, the lower vessel half 16 is inverted so that its weight and the weight of the pressure fluid therein is supported by the base enclosure 20. Since the vessel plate 38 and its connecting skirt 36 are already designed for supporting the full weight of the assembled vessel, an alternate form of the invention supports the vessel portion 16 on its vessel base 38, with the base enclosure 20 this time being at the top of the assembly.

The height B of the base ring cylinder should be high enough so that fixed end effects of the base plate do not effect the motions and stresses at the cylinder to vessel junction 14, 24. The structural effects at this junction should simulate the rotations and deflections of a full vessel joint for an assembled vessel.

One critical requirement of the present invention is that the base ring of the base enclosure be sufficiently high to effectively restrict any vessel dilation at the open end of the vessel portion which was formed when the vessel was fabricated or divided. For large pressure vessels of the type to be tested according to the present invention, the height of the vessel half shown at A in FIG. 3 may be on the order of 50 feet with the diameter C on the order of 60 feet. With vessels of this size, it has been found that the maximum height B of the base ring and the base enclosure can be calculated as follows:

$$L_{MAX} = 2.5 \sqrt{Rt} \quad (1)$$

where:
R is the radius of the vessel;
t is the wall thickness of the vessel; and
$L_{MAX}$ is the maximum height where it is assumed all end effects are dampened out.

Shorter heights may be calculated with the most economical height chosen for the height of the base ring.

A representative lower limit for the base ring height may be as follows:

$$L_{MIN} = 1.5 \sqrt{Rt} \quad (2)$$

For a 60 foot diameter vessel, $L_{MAX}$ may be approximately 10 feet with a wall thickness of approximately 6 inches assumed. For the same vessel dimensions and wall thickness, LMIN may be approximately 6 feet.

Figure 4:
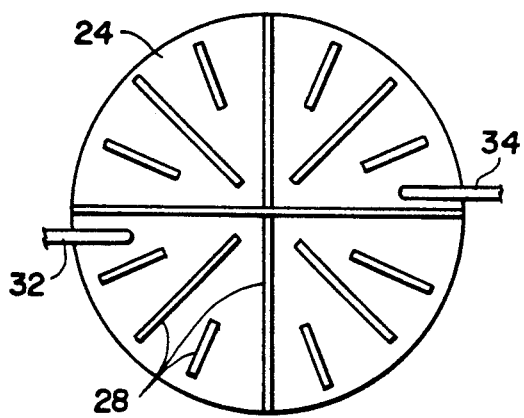
FIG. 4 is a bottom plan view of a base enclosure with support beams laid out in accordance with one embodiment of the invention.
Figure 5:
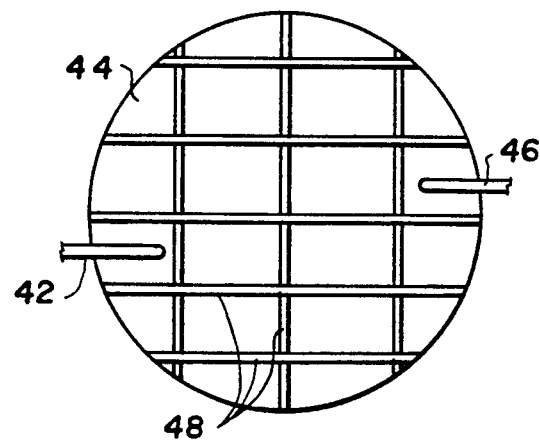
FIG. 5 is a view similar to FIG. 4 of a further embodiment of the invention.

FIG. 4 illustrates the support means of the invention which include a radial distribution of support beams 28 welded to the bottom of base plate 24. As shown in FIG. 5, an alternate form of the invention may utilize a grid pattern of support beams 48 welded to the bottom of a base plate 44. Both beam patterns of FIGS. 4 and 5 allow for convenient positioning of the inlet and outlet conduits 32, 34 in FIG. 4 and 42, 46 in FIG. 5.

Figure 6:
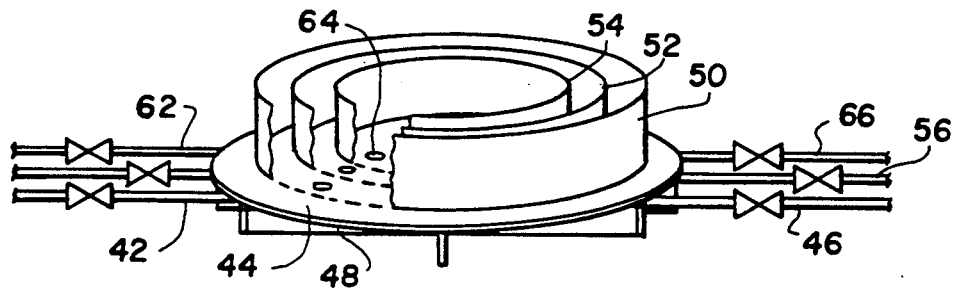
FIG. 6 is a perspective view of a base enclosure according to the present invention which is constructed to permit the testing of vessels having different radii.

FIG. 6 shows an embodiment of the invention which is designed for use with a variety of vessel diameters. A maximum vessel diameter can be serviced by welding the open end of the vessel half to the upper edge of an outer base ring 50. Pressure fluid may be supplied by an inlet conduit 42 and drained by an outlet conduit 46 with appropriate valves provided. Smaller diameter base rings 52 and 54 which are also welded to the top of base plate 44 can be used for servicing smaller diameter vessels which may each include their own inlet/outlet conduits. Alternatively, a conduit 62 connected to an inlet opening 64 in the smallest diameter base ring 54 may be used in conjunction with multiple outlet conduits 46, 56 and 66 which include valves and are connected to outlet openings in the respective base rings 54, 52 and 50. While the inner inlet 64 will fill the entire volume of the base assembly plus vessel portion combination, whether large diameter or small diameter vessels are to be tested, separate drains are needed to avoid trapped fluid within the spaces between the base rings.

According to the present invention, the large vessel height is reduced by one half for the pressure test. Because of this, the fabricated or divided vessel portions are advantageously transported with or without the base enclosure. Assembly or reassembly of the vessel should take place at the site where the vessel will ultimately be used. This eliminates the waste of cutting shell material away and reprepaing the cylinder which is currently required. Not only is the outer dimension reduced but also weight is reduced for the individual vessel portions for shipping.

While specific embodiments of the invention have been shown and described in detail to illustrate the application of the principles of the invention, it will be understood that the invention may be embodied otherwise without departing from such principles.

What is claimed is:

1. A method of pressure testing a large vessel, comprising:
   fabricating or dividing the vessel into a first portion having one closed end and an opposite open end, and a second portion having one closed end and an opposite open end;
   attaching a first base enclosure to the open end of the first portion for closing the open end of the first portion;

attaching a second base enclosure to the open end of the second portion for closing the open end of the second portion;

separately pressure testing the first and second portions of the vessel;

subsequently disconnecting the first and second base enclosures from the first and second portions respectively for reopening the open ends of the first and second portions; and connecting or reconnecting the first and second portions of the vessel at their open ends for assembling the vessel.

2. A method according to claim 1 including fabricating or dividing the vessel in approximately half portions for forming a first vessel portion and a second vessel portion.

3. A method according to claim 1 wherein each of the base enclsoures is reusable and comprises a cylindrical base ring having a diameter substantially equal to the diameter of the vessel, the ring having an upper edge and a lower edge, a base plate connected to the lower edge of the base ring, and support means connected to the base plate for supporting the weight of the base enclosure, the vessel portion attached thereto and pressure fluid in the vessel portion for pressure testing the vessel portion, the method including attaching the upper edge of the base ring to the open end of the vessel portion to be tested.

4. A method according to claim 3 including attaching the first base enclosure to the first vessel portion and the second base enclosure to the second vessel portion by welding.

5. A method according to claim 1 including attaching the first base enclosure to the first vessel portion and the second base enclosure to the second vessel portion by welding.

6. A method according to claim 1 including pressure testing the first and second portions of the vessel by admitting a pressure fluid into each base enclosure and thereafter draining the pressure fluid through each base enclosure.

7. A method according to claim including transporting the vessel to a site where it is to be used before the first and second portions are assembled or reassembled with each other.

8. An apparatus for pressure testing a large vessel, comprising:

a base ring having an upper edge adapted to be attached to an open end of a vessel portion for pressure testing the vessel portion, the base ring having a lower edge;

a base plate connected to the lower edge of the base ring to form a base enclosure with the base ring;

inlet/outlet means connected to the base enclosure for admitting and releasing pressure fluid into and out of the base enclosure for pressure testing a vessel portion attached to the base ring; and support means connected to the base plate for supporting the weight of the base enclosure, a vessel portion to be pressure tested and a fluid contained in the vessel portion to be pressure tested.

9. An apparatus according to claim 8 wherein the base ring has a radius the vessel portion tested using the base ring has a wall thickness, and the base ring has a maximum height above the base plate equal to $2.5\sqrt{Rt}$, where R is equal to the radius of the base ring and t is the wall thickness of the vessel.

10. An apparatus according to claim 9 wherein the base ring has a minimum height above the base plate equal to $1.5\sqrt{Rt}$.

11. An apparatus according to claim 8 wherein the support means comprises a pattern of beams fixed to a lower surface of the base plate.

12. An apparatus according to claim 11 wherein the pattern of beams comprises a radial pattern of beams.

13. An apparatus according to claim 11 wherein the pattern of beams comprises a grid pattern of beams.

14. An apparatus according to claim 8 including the base enclosure having an interior and wherein the inlet/outlet means comprises at least one inlet conduit opening through the base plate into the interior of the base enclosure and at least one outlet conduit opening through the base plate into the interior of the base enclosure.

15. An apparatus according to claim 8 including a plurality of base rings each with a different diameter, and each connected to said base plate for vessels having different diameters.

16. An apparatus according to claim 15 wherein the base rings are welded to the base plate.

17. An apparatus to claim 16 wherein the base rings are temporarily welded to the base plate for forming a reusable base enclosure.

18. An apparatus according to claim 8 wherein the base ring is temporarily welded to the base plate for forming a reusable base enclosure.

* * * * *